(12) United States Patent
Sobral et al.

(10) Patent No.: US 8,445,471 B2
(45) Date of Patent: May 21, 2013

(54) PROCESS FOR OBTAINING STEROIDAL PHOSPHATE COMPOUNDS

(75) Inventors: Luis Sobral, Loures (PT); Filipe Gaspar, Santo Amaro de Oeiras (PT); William Heggie, Palmela (PT); Emilia Leitao, Cacem (PT); Jose Rafael Antunes, Setubal (PT)

(73) Assignee: Hovione Inter Limited, Lucerne (CH)

( * ) Notice: Subject to any disclaimer, the term of this patent is extended or adjusted under 35 U.S.C. 154(b) by 492 days.

(21) Appl. No.: 12/600,311

(22) PCT Filed: May 16, 2008

(86) PCT No.: PCT/GB2008/001709
§ 371 (c)(1),
(2), (4) Date: Jun. 4, 2010

(87) PCT Pub. No.: WO2008/139210
PCT Pub. Date: Nov. 20, 2008

(65) Prior Publication Data
US 2010/0240916 A1    Sep. 23, 2010

(30) Foreign Application Priority Data

May 16, 2007 (PT) .......................... 103743

(51) Int. Cl.
*A61K 31/573* (2006.01)
*C07J 1/00* (2006.01)

(52) U.S. Cl.
USPC ........................... 514/179; 514/180; 552/507

(58) Field of Classification Search
USPC .................. 552/507; 514/179, 180
See application file for complete search history.

(56) References Cited

FOREIGN PATENT DOCUMENTS

GB            952193         3/1964

OTHER PUBLICATIONS

PCT International Preliminary Report, PCT/GB2008/001709 filed May 16, 2008, dated Aug. 28, 2009.
PCT International Search Report, PCT/GB2008/001709 filed May 16, 2008, dated Feb. 27, 2009.
Nurnberg, E. et al., "Darstellung Polymorpher Modifikationen des Betamethasonacetats," Pharm. Ind., 1988, vol. 50, No. 9, pp. 1085-1090, XP008102070, To the extent discussed by the international agency.
Steckel, H. et al., "In Vitro Characterization of Jet-Milled and In-Situ-Micronized Fluticasone-17-Propionate," International Journal of Pharmaceutics, 2003, vol. 258, pp. 65-75, XP002515868.
Tsotsas, E. et al., "Drying of Solid Materials," Ullman's Encyclopedia of Industrial Chemistry, 2005, pp. 1-36, Retrieved from the Internet: URL: 10.1002/14356007.b0204, XP002515869.
Nurnberg, E., "Kolloide Verteilungszustande in der Pharmazeutischen Technologie: Herstellung and Eigenschaften Pharmazeutischer Praparate durch Spruhtrocknung," Progr. Colloid & Polymer Sci., 1976, vol. 59, pp. 55-69, XP008102337, To the extent discussed by the international agency.

*Primary Examiner* — Barbara P Badio
(74) *Attorney, Agent, or Firm* — MacMillan, Sobanski & Todd, LLC

(57) ABSTRACT

A process for obtaining 21-disodium phosphate pregnane derivative compounds of formula (I), wherein X=R=H or X=F and R=α-$CH_3$ or X=F and R=β-$CH_3$: comprises spray drying a solution comprising compound of formula (I).

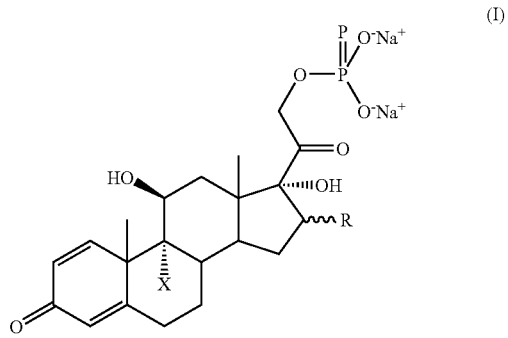

(I)

30 Claims, 3 Drawing Sheets

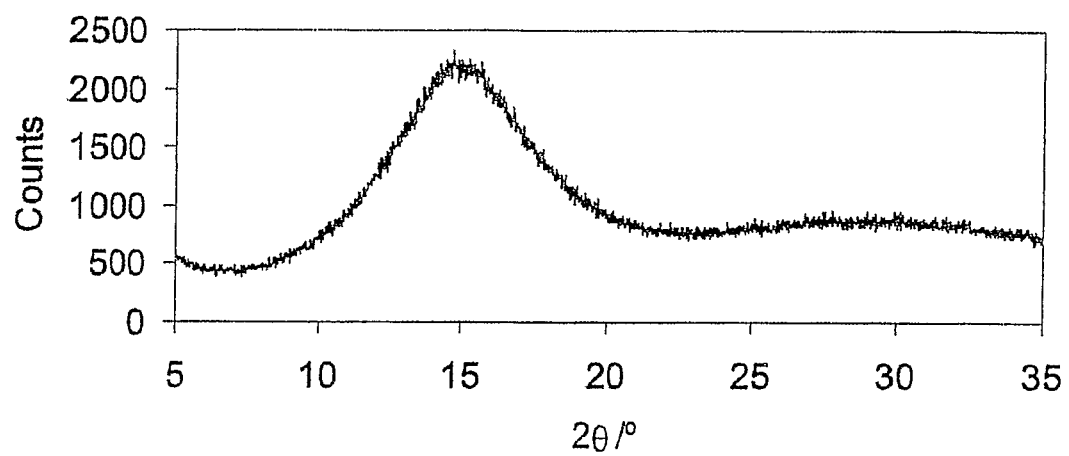
Fig. 1. XRPD of spray dried betamethasone 21-disodium phosphate

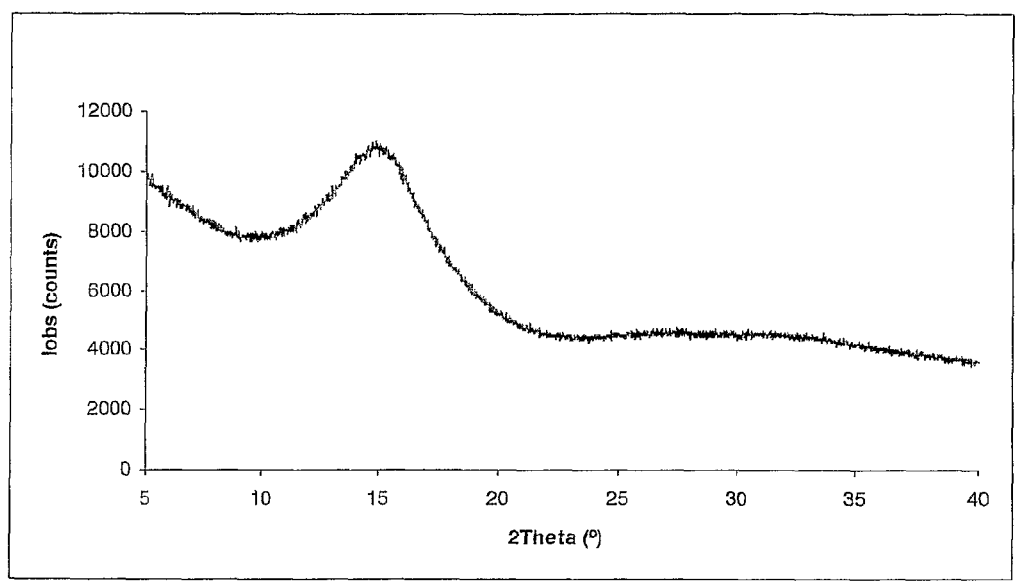
Fig. 2. XRPD of spray dried dexamethasone 21-disodium phosphate

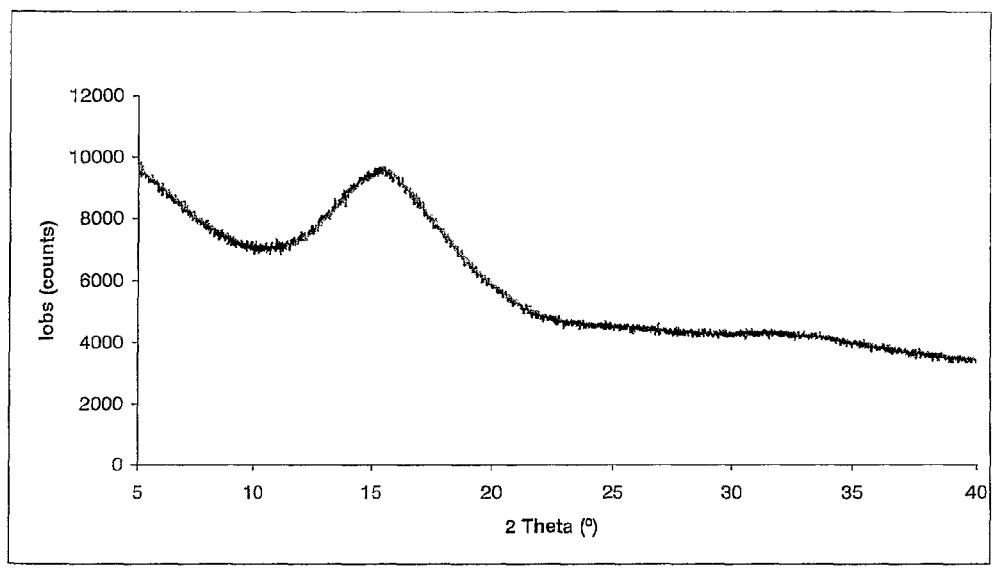
Fig. 3. XRPD of spray dried prednisolone 21-disodium phosphate

PROCESS FOR OBTAINING STEROIDAL PHOSPHATE COMPOUNDS

The present invention claims the benefit of the PCT/GB08/001709 filed May 16, 2008, which claims priority to PT Ser. No. 103.743, filed May 16, 2007.

The present invention relates to a process for preparing 21-disodium phosphate pregnane derivatives, and to compounds so prepared and their use in medicine.

The present invention relates to a new process for obtaining 21-disodium phosphate pregnane derivative-compounds of formula [I], wherein X=R=H or X=F and R=α-CH₃ or X=F and R=β-CH₃,

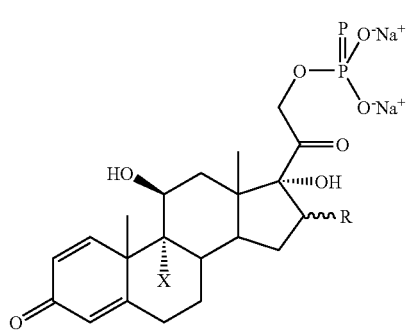

DESCRIPTION OF THE INVENTION

The present invention relates to a new process for obtaining preferably solid 21-disodium phosphate pregnane compounds of formula [I] which comprises spray drying a solution containing compound of formula [I]. Preferably, the solvent is water, wherein the concentration of the solution is preferably from 2% to 30% w/w, even more preferably 3% to 5%.

A particular feature of this invention is that the process herein disclosed minimises degradation of the 21-disodium phosphate pregnane compounds during drying, thus yielding compound [I] with a high purity. It is well known that fast degradation of these sodium phosphate salts occurs. For example, when storing betamethasone 21-phosphate at a temperature of 40° C. and a relative humidity of 75% after one month high levels of decomposition products are observed, signifying that the products no longer complies with Pharmacopoeia monographs.

Another aspect of this invention is that a process is provided wherein the compounds of formula [I] are obtained in the form of an amorphous solid.

One further aspect of the invention herein disclosed is that is that the process described to obtain solid compounds of formula [I], is easily scaled up and can be applied at an industrial scale. In particular, solid betamethasone 21-disodium phosphate, [I] where R=β-CH₃ and X=F, can be obtained on a large scale by spray drying as described hereinbelow. Solid dexamethasone 21-disodium phosphate [I] where R=α-CH₃ and X=F, and prednisolone di-sodium phosphate [I] where R=X=H and other similar derivatives may be prepared by the same method.

PRIOR ART

Betamethasone 21-disodium phosphate is a synthetic corticosteroid having activity as an anti-inflammatory which is used to treat conditions such as arthritis, dermatitis and allergies. GB 913,941 discloses the preparation of 21-phosphate derivatives of 16β-alkyl-11-oxygenated-17α,21-dihydroxy-3,20-diketo-1,4-pregnadienes, Betamethasone 21-sodium phosphate included, by following the synthetic route represented in scheme I.

Scheme 1. Synthetic route disclosed in GB 913,941.

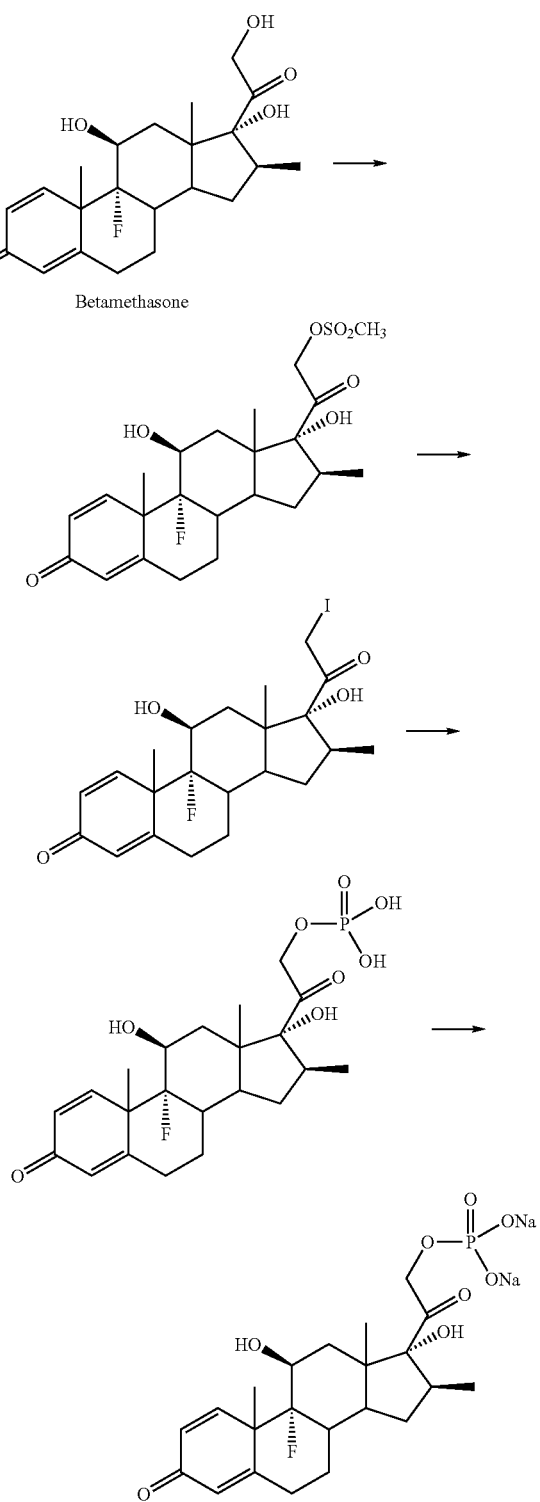

GB 913,941 does not teach how to obtain the 21-phosphates sodium derivatives as solids.

GB 952,193 discloses a process for the manufacture of steroid-21-orthophosphates [VII] and their physiologically compatible water-soluble salts by treatment of the diamido group of steroid 21-diamido-orthophosphates [VI] with an acidic reagent.

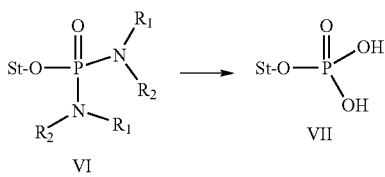

The steroid 21-orthophosphates is prepared by treatment of the corresponding steroid 21-diamido.orthophosphates with mineral acids or strong organic acids such as organic sulphonic acids. The corresponding water soluble salts are obtained by treatment of the steroid 21-orthophosphates with caustic alkali, alkali metal hydrogen carbonate or alkali metal carbonate. The salts are dried under reduce pressure.

A shorter route of synthesis is described in GB 1,148,453 which claims a process for preparing 21-phosphates of a "corticoid-type" by reaction of a 21-hydroxy "corticoid-type" steroid with pyrophosphoryl tetrachloride followed by hydrolysis.

Scheme 2. Synthetic route disclosed in GB 1,148,453.

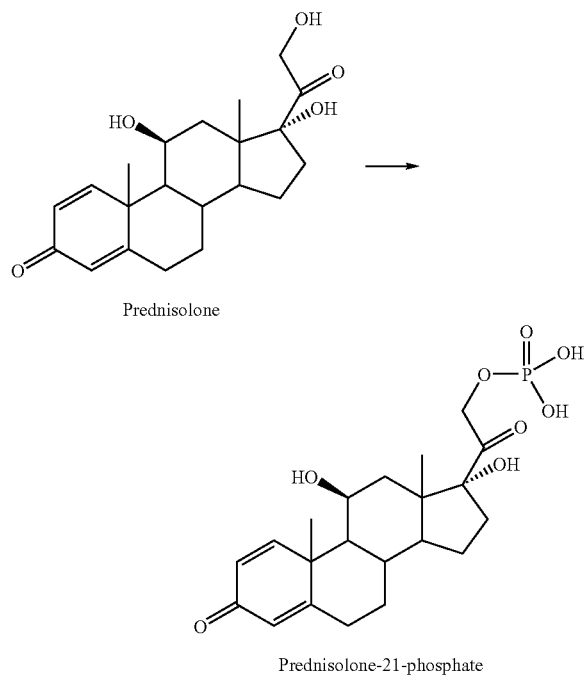

The 21-phosphate is isolated by freeze drying or by evaporation of the solvent under reduced pressure.

PT55887 claims a process to prepare 21-phosphate of 16β-methyl-9α-fluoro-prednisolone by reaction of 21-Diiodo-16β-methyl-9α-fluoro-11β,17α-dihydroxy-1,4-pregandi-ene-3,20-dione with o-phosphoric acid in the presence of a sodium or potassium salt of that acid or of a tertiary amine. The sodium salt of the phosphate is prepared by neutralization of the 21-phosphate with sodium hydroxide.

Scheme 2. Route of Synthesis disclosed in PT55887.

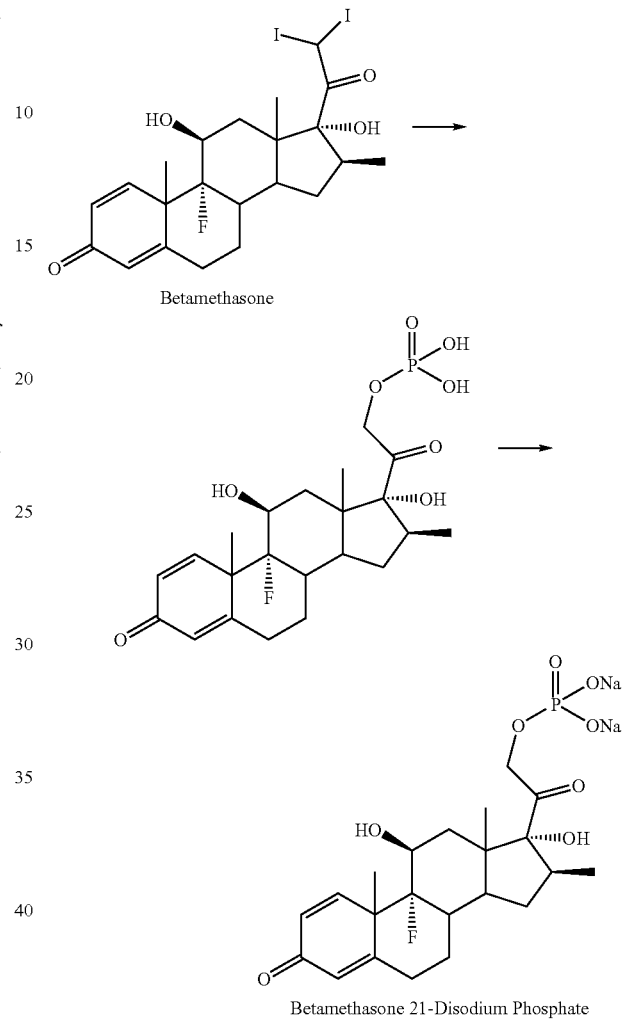

However, PT 55887 contains no teaching as to how to dry the sodium salt of the phosphate.

U.S. Pat. No. 2,779,775 claims compounds phosphate derivatives of 9α-fluoro steroids and also claims processes to obtain those compounds. It does not, however, disclose details on how to dry the phosphate compounds.

U.S. Pat. No. 2,932,657 claims processes to purify steroid phosphate esters, more particularly processes for recovering such esters in pure form from reaction mixtures contaminated with inorganic compounds. The phosphate esters are dried under vacuum at temperatures from 25° C. and 60° C.

U.S. Pat. No. 3,966,778 claims the production of 21-phosphate corticoids having unprotected hydroxyl groups radicals at least at the 17α and 21-position. The phosphate corticoids are isolated by evaporation of the solvents under reduced pressure.

U.S. Pat. No. 2,939,873 claims a process for producing tertiary lower alkyl amine salts of unsaturated pregnane-21-dihydrogen phosphate esters having a general formula [IV] and [V], where R1 is selected from the groups:

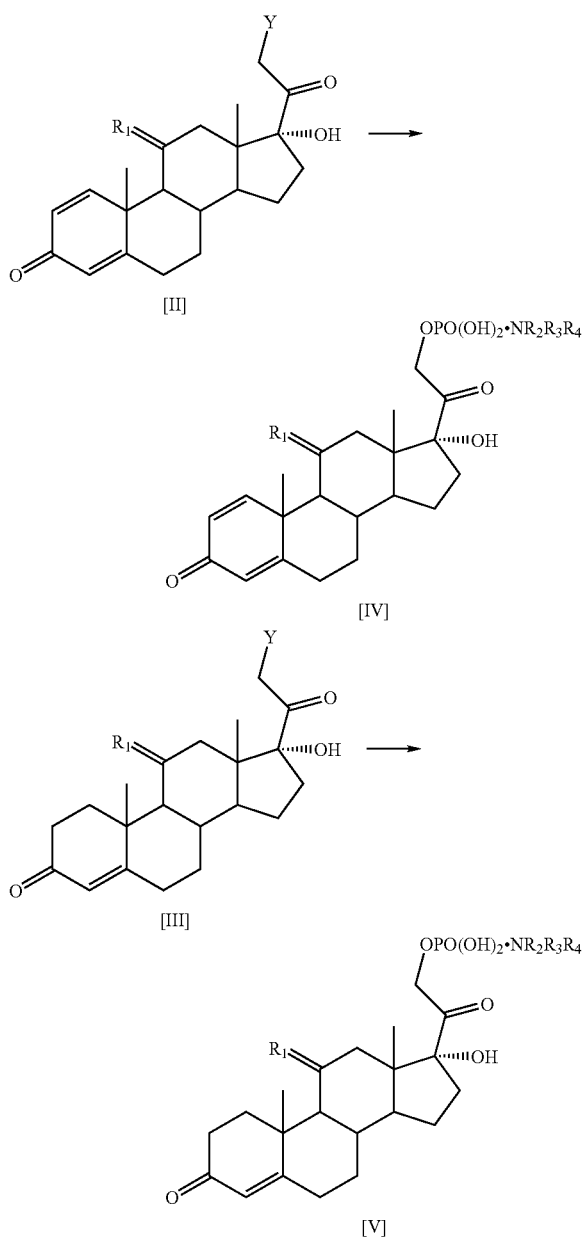

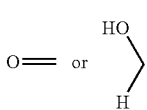

and R2, R3 and R4 are lower alkyl radicals, which comprises combining the corresponding starting materials [II] and [III], wherein R1 is as previously defined, and Y is a radical selected from the group consisting of halogens with an atomic weight of at least 35 and lower hydrocarbon sulfonyloxy radicals of the formula $OSO_2R5$ where R5 is a hydrocarbon radical containing from one to 10 carbon atoms, with a tertiary lower alkyl amine phosphate. The steroid phosphate amine salts are converted to the corresponding steroid dihydrogen phosphate free acids and alkali metal salts thereof. Conversion to the dihydrogen phosphate is effected by contact of a solution of the steroid phosphate amine salt with a strongly acidic anion exchange resin in its hydrogen form. The sodium salt is prepared by reaction of the phosphate free acid with sodium hydroxide or with a methanolic solution of sodium methoxide and is air-dried.

Processes for preparing phosphate derivatives of Cortisone and Hydrocortisone are claimed in U.S. Pat. No. 3,068,223 where the phosphate group is introduced into the 21 position of the steroid by reaction of the 21-Iodo derivative with silver dibenzylphosphate. This patent states that the salts of the 21-phosphate cortisone or hydrocortisone may be prepared by reacting the compound with an aqueous solution of alkali or alkaline bases or salts such as hydroxides, carbonates, bicarbonates or acetates. The sodium salt of cortisone phosphate is dried in air and no further details are given on how to dry the other salts.

According to the present invention, there is provided a process for obtaining steroidal 21-disodium phosphate compounds of formula [I], which process comprises spray drying a solution comprising a compound of formula [I].

Any suitable solvent may be used in the solution. It is preferable that the solution comprises a solvent which is water or a mixture of water and a water-miscible organic solvent. Preferably, the solvent consists of water.

Preferably, the compound of formula [I] is betamethasone 21-phosphate or prednisolone 21-phosphate or dexamethasone 21-phosphate.

The solution preferably comprises a solvent which is water.

It is preferable that the concentration of the compound of formula [I] in the solution is between 2% w/w and 30% w/w, more preferably the concentration of the compound of formula [I] in the solution is between 3% w/w and 5% w/w.

Preferably, the solution is spray dried at a drying temperature of 105° C. or below. More preferably, the drying temperature is from 80 to 100° C. A drying temperature of about 85° C. is particularly preferred.

It is preferable that the pH of the solution is below pH 9. More preferably, the pH of the solution is from pH7.6 to pH7.9

The present invention also provides amorphous solid compound of formula [I] wherein X=F and R=β-$CH_3$.

The present invention also provides amorphous solid steroidal 21-disodium phosphate compounds of formula [I], obtainable by a process comprising spray drying a solution comprising a compound of formula [I].

The present invention also provides amorphous solid compounds of formula [I] wherein X=R=H or X=F and R=α-$CH_3$ or X=F and R=β-$CH_3$.

The present invention also provides amorphous solid compounds of formula [I] wherein X=R=H or X=F and R=α-$CH_3$ or X=F and R=β-$CH_3$ obtainable by a process comprising spray drying a solution comprising a compound of formula [I].

It is preferable that the amorphous solid compounds of formula [I] provided by the invention comprise degradation products at a level below 0.10% (HPLC area %). Most preferably, the amorphous solid compound of formula I comprising degradation products below 0.10% is betamethasone 21-phosphate.

It is preferred that the amorphous solid compounds of formula [I] are essentially free of solvates of the compound of formula [I] with organic solvents. By "essentially free" we refer to amorphous solid compounds of formula [I] which comprise less than 1%, preferably less than 0.5%, more preferably less than 0.2%, even more preferably less than 0.1% or 0% of solvates of the compound of formula [I] with organic solvents.

According to the present invention, there are also provided compounds of formula [I] obtainable by the methods of the invention, preferably solid amorphous compounds of formula [I], for use as a medicament.

The present invention also provides pharmaceutical formulations comprising compounds of formula [I] obtainable by the process of the invention.

DETAILED DESCRIPTION OF THE INVENTION

This invention provides a process comprising spray drying a solution containing a compound of formula [I]. Advantageously, the process of the present invention prevents degradation of the compound during isolation of solid material.

The compound of formula [I] can be dissolved in a suitable solvent, such as water, and the solvent can be safely evaporated in a spray drying equipment. Any suitable solution concentration can be used. However, a solution concentration of 2-30% w/w is preferred, even more preferably the solution has a concentration of 3% to 5% w/w. By "% w/w" we mean the mass of the compound of formula [I] as a percentage of the mass of the total solution. The concentration to be employed will generally be limited by the solubility of [I] in the solvent. Water is a preferred solvent since it is a non toxic solvent which can be handled without special health and safety concerns. In addition, the residual level of water in the final product can be as high as 10% w/w.

Spray drying may be performed using any suitable equipment, for example, using equipment that is commercially available. Any suitable drying gases can be used, such as, for example, air or nitrogen. A variety of atomisation methods can be used, depending, for instance, on the equipment being used. For example, a pneumatic spray nozzle orifice of 0.7 mm is suitable although alternate atomization methods such as rotary, pressure and ultrasonic nozzles can be used in a variety of equipment. The preferential atomization gas flow in terms of normal liters per hour can be adjusted to the equipment in use and any suitable atomisation gas flow can be used. Typically, for a smaller scale unit, 357 to 670 liters per hour is preferred. In a preferred embodiment, the nozzle assembly can be cooled with a suitable fluid during spray drying to minimize product degradation.

Any suitable drying temperature can be used. Drying temperatures involved in the spray drying of the aqueous solution of compound of formula [I] are typically those employed in the spray drying of aqueous feedstocks. For example, preferably outlet temperatures range from 65° C. to 108° C. but are more preferably 80-100° C.

Any suitable solution flow rate can be used. Solution flow rate may preferably be from 1 to 20 ml/min, more preferably from 3 to 9 ml/min for the 0.7 mm nozzle.

Inlet temperature may be adjusted to attain a suitable range of outlet temperatures. For example, the inlet temperature can be from 80 to 200° C.

In a particularly preferred embodiment, the outlet temperature, atomization flow rate, solution concentration and solution flow rate, among other tested parameters, can be combined in order to obtain compound [I] complying with the European Pharmacopoeia (EP) and United States Pharmacopoeia (USP). In particular, the above parameters may be combined in order to achieve the required limits for residual solvents and related substances. For example, the concentration of the solution has been found to have opposite effects on the level of water and on the level volatile solvents in the spray dried product. An increase in solution concentration was observed to result in an increase in the content of volatile solvents and a decrease in the level of water. The best compromise was found to be with a solution concentration of about 5% w/w. At this concentration level, betamethasone 21-sodium phosphate obtained by spray drying, with an outlet temperature of 85° C. and an atomization gas flow of 357 normal liters per hour and a solution flow rate of 6 ml/min, had a water content of 7.9% w/w and a total content of volatile solvents below 3000 ppm. Accordingly, these conditions are particularly preferred, but not essential.

The outlet temperature and the pH of the solution may affect the purity of the spray dried product. For example, outlet temperatures above 105° C. may promote significant degradation. Accordingly, it is preferred to use outlet temperatures of about 80° C. to about 100° C. An outlet temperature of 85° C. is particularly preferred. Similarly, the spray drying of solutions with a pH of about 9 may lead to higher levels of degradation. Accordingly, it is preferred to have a solution pH of below about pH 9, suitably below pH 8. Even more preferably, the pH of the solution to be spray dried may be 7.6 to 7.9. If the pH of the solution is outside this range then it may preferably be adjusted by addition of any suitable acid or alkali, for example, an acid such as dilute hydrochloric acid.

One disadvantage of drying compound [I] according to known methods such as the use of a fluidized bed drier is that severe decomposition of the compound of formula [I] during drying may occur. Decomposition is observed at temperatures equal to or higher than 40° C. and occurs either under vacuum or under nitrogen atmosphere. A typical degradation product is betamethasone along with unknown related substances, which are detected by high performance liquid chromatography (HPLC).

Betamethasone

Surprisingly, spray drying compound [I], R=βCH3 and X=F, according to the process of the present invention allows drying of the product in a controlled way so that the dried betamethasone 21-disodium phosphate thus obtained contains desirable levels of degradation products such as Betamethasone and related substances, for example levels of degradation products below 0.10% (HPLC area %).

Another disadvantage of the known methods is that sometimes compound [I], wherein R=βCH3 and X=F, may precipitate as a solvate of organic solvents such as methanol or acetone, retaining a level of solvents higher than those allowed by International Guidelines and Pharmacopoeias making the product unsuitable for pharmaceutical applications. When drying compound [I], wherein R=βCH3 and X=F, using the process according to the present invention, solvates of organic solvents such as methanol and or isopropanol are not formed and the compound [I], for example, Betamethasone 21-Disodium Phosphate, obtained complies with Pharmacopoeia limits for residual solvents.

The compounds of formula [I] so obtained using the method of this invention are amorphous solids.

BRIEF DESCRIPTION OF THE DRAWINGS

FIG. 1, FIG. 2 and FIG. 3 depict the X-ray powder diffraction patterns of betamethasone 21-disodium phosphate, of dexamethasone 21-phosphate and of prednisolone 21-phosphate, respectively, obtained from spray drier according to the process herein disclosed. These XRPD diffraction patterns have a broad, diffuse and low intensity peak which is characteristic of an amorphous material.

Compound [I] employed in the present invention may be prepared by any known process.

Examples 1, 2 and 3 illustrate the invention and certain preferred embodiments and are not intended to limit the scope of the invention. The experiments reported were carried out using a BUCHI model B-290 Advanced spray dryer, with a spray orifice of two fluid nozzle with 0.7 mm orifice diameter.

EXAMPLE 1

Spray Drying of Betamethasone 21-disodium Phosphate

Wet betamethasone 21-disodium phosphate obtained by applying literature techniques and having a purity of 99.8% (HPLC area %) was dissolved in water to give a 5% w/w solution based on dry material. The pH of the solution was adjusted to 7.6/7.9 by addition of hydrochloric acid 1N. The outlet temperature was kept between 80° C. and 100° C., the atomization flow was between 357-670 normal liters per hour and the solution flow rate was between 5 ml/min and 9 ml/min. The product was collected in a high performance cyclone. The product [betamethasone 21-phosphate] was obtained with a purity of 99.6% and with residual solvents complying with USP and EP Pharmacopoeias (Methanol: 428 ppm; Isopropanol: 2088 ppm; Water, by Karl-Fischer: 8.0% w/w).

EXAMPLE 2

Spray Drying of Dexamethasone 21-disodium Phosphate

Dexamethasone 21-disodium phosphate with a purity of 99.2% (HPLC area %) was dissolved in water to give a 5% w/w solution. The pH of the solution was adjusted to 7.6/7.9 by addition of hydrochloric acid 1N. The outlet temperature was kept between 80° C. and 100° C., the atomization flow was between 357-670 normal liters per hour and the solution flow rate was between 5 ml/min and 9 ml/min. The product was collected in a high performance cyclone. The product [dexamethasone 21-phosphate] was obtained with a purity of 99.2% (HPLC area %).

EXAMPLE 3

Spray Drying of Prednisolone 21-disodium Phosphate

Prednisolone 21-disodium phosphate with a purity of 98.4% (HPLC area %) was dissolved in water to give a 5% w/w solution. The pH of the solution was adjusted to 7.6/7.9 by addition of hydrochloric acid 1N. The outlet temperature was kept between 80° C. and 100° C., the atomization flow was between 357-670 normal liters per hour and the solution flow rate was between 5 ml/min and 9 ml/min. The product was collected in a high performance cyclone. The product [prednisolone 21-phosphate] was obtained with a purity of 99.2% (HPLC area %).

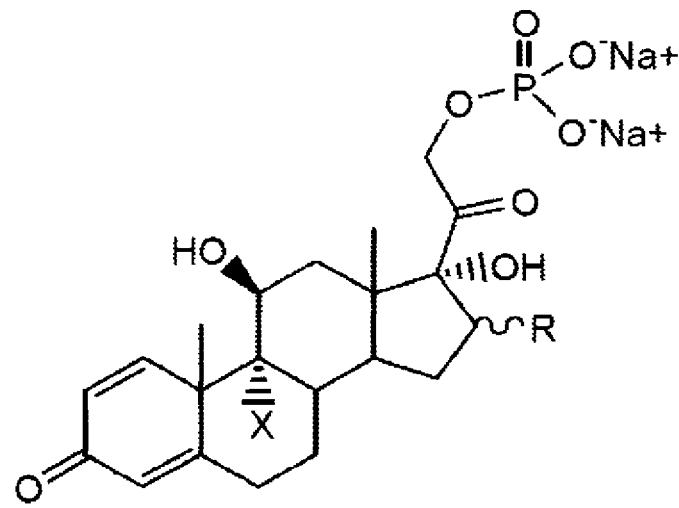

The invention claimed is:

1. A process for obtaining steroidal 21-disodium phosphate compounds of formula

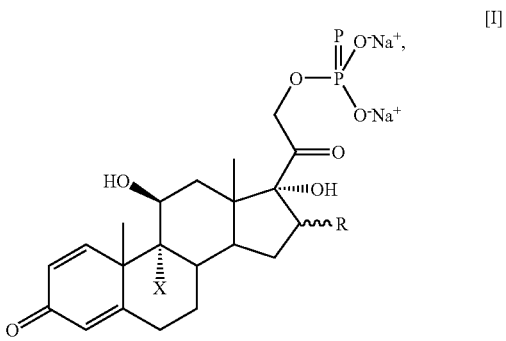

comprising about 0.10% or below (HPLC area %) of degradation products, wherein X=R=H or X=F and R=αCH$_3$ or X=F and R=β-CH$_3$, which process comprises spray drying a solution comprising a compound of formula [I].

2. A process according to claim 1 wherein the compound of formula [I] is betamethasone 21-phosphate.

3. A process according to claim 1 wherein the compound of formula [I] is prednisolone 21-phosphate.

4. A process according to claim 1 wherein the compound of formula [I] is dexamethasone 21-phosphate.

5. A process according to claim 1 wherein the solution comprises a solvent which is water or a mixture of water and a water-miscible organic solvent.

6. A process according to claim 5 wherein the solvent consists of water.

7. A process according to claim 5 wherein the concentration of the compound of formula [I] in the solution is from about 2% w/w to about 30% w/w.

8. A process according to claim 7, wherein the concentration of the compound of formula [I] in the solution is from about 3% w/w to about 5% w/w.

9. A process according to claim 1 wherein the solution is spray dried at a drying temperature of about 105° C. or below.

10. A process according to claim 9, wherein the drying temperature is from about 80 to about 100° C.

11. A process according to claim 10, wherein the drying temperature is about 85° C.

12. A process according to claim 1 wherein the pH of the solution is about pH 9 or below.

13. A process according to claim 12, wherein the pH of the solution is from about pH 7.6 to about pH 7.9.

14. A process according to claim 1 wherein the pH of the solution is about pH 9.

15. Amorphous solid compounds of formula [I] obtained by the process according to claim 1, which are essentially free of solvates of the compound of formula [I] with organic solvents.

16. Amorphous solid compound of formula [I] according to claim 15, wherein X=F and R=β-CH$_3$.

17. Amorphous solid compound of formula [I] according to claim 15 comprising about 0.10% or below (HPLC area %) of degradation products.

18. The compound of claim 15, wherein the compound comprises about 0.10% (HPLC area %) of degradation products.

19. A pharmaceutical formulation comprising a compound of formula [I] according to claim 15.

20. A process according to claim 1, further comprising converting a compound of formula [I] which are essentially free of solvates of the compound of formula [I] with organic into a medicament.

21. A process for obtaining steroidal 21-disodium phosphate compounds of formula

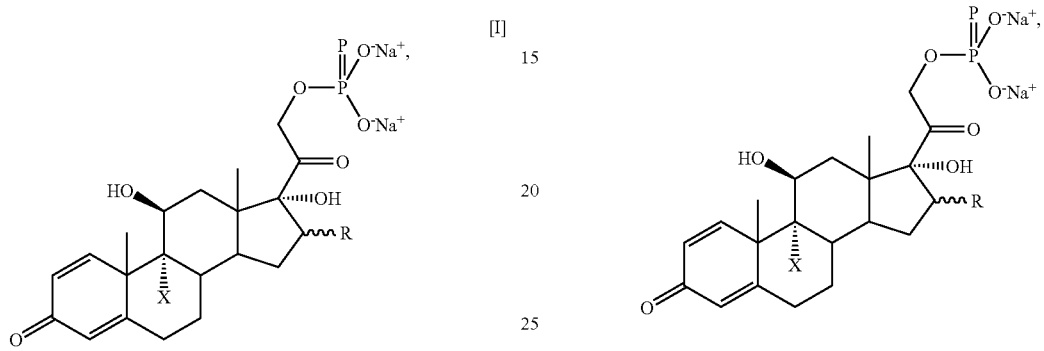

wherein X=R=H or X=F and R=α-$CH_3$ or X=F and R=β-$CH_3$, which process comprises:
spray drying a solution comprising a compound of formula [I] and a solvent which is water or a mixture of water and a water-miscible organic solvent, the concentration of the compound of formula [I] in the solution being from about 2% w/w to about 30% w/w, and the pH of the solution being about pH 9 or below, and
spray drying at a drying temperature of about 105° C. or below sufficient to form an amorphous solid compound of formula [I], the amorphous solid compound comprising about 1% or below of solvates of the compound of formula [I].

22. The process of claim 21, wherein the pH of the solution is from about pH 7.6 to about pH 7.9; the solvent consists of water; the concentration of the compound of formula [I] in the solution is from about 3% w/w to about 5% w/w; the drying temperature is from about 80 to about 100° C.; and wherein the amorphous solid compound comprising about 0.5% or below of solvates of the compound of formula [I].

23. The process of claim 21, wherein the amorphous solid compound comprises about 1% of solvates of the compound of formula [I].

24. The process of claim 22, wherein the amorphous solid compound comprises about 0.5% of solvates of the compound of formula [I].

25. Amorphous solid compounds of formula [I] obtained by the process according to claim 21.

26. An amorphous solid compound of formula [I]

wherein X=R=H or X=F and R=α-$CH_3$ or X=F and R=β-$CH_3$, comprising about 1% or less of solvates of the compound of formula [I].

27. The amorphous solid compound of claim 26, wherein the compound is: betamethasone 21-phosphate compound having a purity of about 99.6% or higher; dexamethasone 21-phosphate having a purity of about 99.2% or higher (HPLC area %); or, prednisolone 21-phosphate having a purity of about 99.2% or higher (HPLC area %).

28. The compound of claim 26, wherein the compound comprises about 1% solvates of the compound of formula [I].

29. The compound of claim 27, wherein the betamethasone 21-phosphate compound has a purity of about 99.6%; the dexamethasone 21-phosphate compound has a purity of about 99.2% (HPLC area %); or, the prednisolone 21-phosphate compound has a purity of about 99.2% (HPLC area %).

30. A pharmaceutical formulation comprising at least the amorphous solid compound of claim 27.

* * * * *

UNITED STATES PATENT AND TRADEMARK OFFICE
CERTIFICATE OF CORRECTION

Page 1 of 2

PATENT NO.        : 8,445,471 B2
APPLICATION NO.   : 12/600311
DATED             : May 21, 2013
INVENTOR(S)       : Luis Sobral et al.

It is certified that error appears in the above-identified patent and that said Letters Patent is hereby corrected as shown below:

In the Claims

Column 10, Claim 1, Lines 10-23, the formula should read --

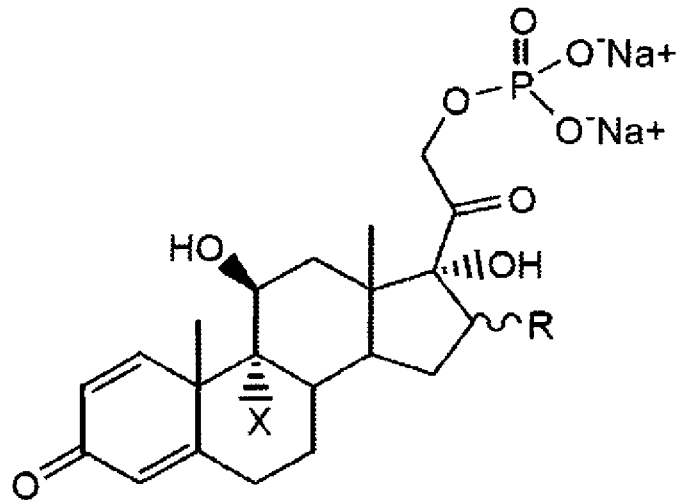

Signed and Sealed this
Third Day of September, 2013

Teresa Stanek Rea
*Acting Director of the United States Patent and Trademark Office*

CERTIFICATE OF CORRECTION (continued)
U.S. Pat. No. 8,445,471 B2

Column 11, Claim 21, Lines 14-27, the formula should read --

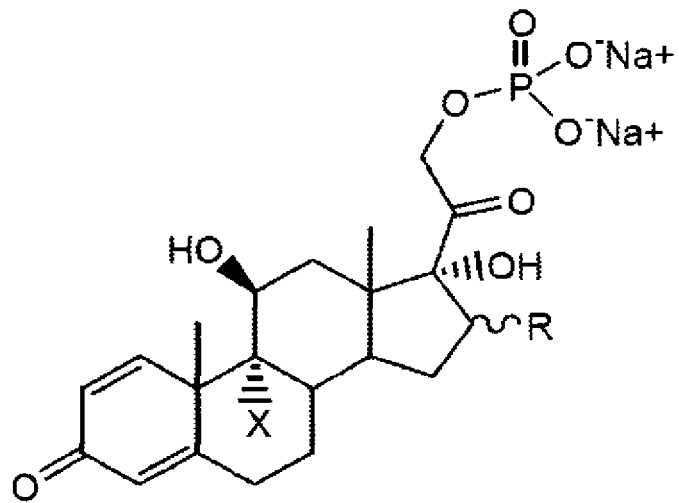

Column 12, Claim 26, Lines 14-26, the formula should read --